United States Patent [19]
Saito

[11] Patent Number: 5,750,795
[45] Date of Patent: May 12, 1998

[54] PROCESS FOR PRODUCTION OF KETONE

[75] Inventor: Noboru Saito, Takatsuki, Japan

[73] Assignee: Nippon Shokubai, Ltd., Osaka, Japan

[21] Appl. No.: 592,684

[22] Filed: Jan. 26, 1996

[30]  Foreign Application Priority Data

Jan. 27, 1995  [JP]  Japan .................................. 7-0315595

[51] Int. Cl.$^6$ ................................................ C07C 45/00
[52] U.S. Cl. ........................... 568/397; 568/319; 568/354
[58] Field of Search ................................... 568/319, 338, 568/354, 397, 325

[56]       References Cited

PUBLICATIONS

Sugiyama et al., Catal. Lett. (1992), 14(1), 127–33, 1992.

*Primary Examiner*—Gary Geist
*Assistant Examiner*—Karl J. Puttlitz, Jr.

*Attorney, Agent, or Firm*—Sherman and Shalloway

[57]              ABSTRACT

The present invention provides a process for producing a ketone represented by a general formula RCOR' (wherein R is a $C_1$–$C_{17}$ alkyl group, a $C_7$–$C_{12}$ aralkyl group, a $C_7$–$C_{12}$ aryl group or a $C_5$–$C_8$ cycloalkyl group; R' is a $C_1$–$C_{17}$ alkyl group, a $C_7$–$C_{12}$ aralkyl group, a $C_7$–$C_{12}$ aryl group or a $C_5$–$C_8$ cycloalkyl group; R and R' may the same), which process comprises reacting a carboxylic acid represented by a general formula RCOOH (wherein R has the same definition as given above) with a carboxylic acid represented by a general formula R'COOH (wherein R' has the same definition as given above) in a gas phase in the presence of a catalyst containing at least either of MgO and CaO.

The process allows for production of an intended ketone at a high yield at high productivity.

7 Claims, No Drawings

PROCESS FOR PRODUCTION OF KETONE

The present invention relates to a process for producing a ketone by subjecting one or two kinds of carboxylic acids to decarboxylation and dehydration in a gas phase in the presence of a catalyst. Ketones are useful as an intermediate in organic synthesis and higher ketones, in particular, are useful as an intermediate for surface active agent, etc.

As an example of the process for synthesis of ketone from carboxylic acid by gas-phase catalytic reaction, there is reported, in Organic Synthesis, Vol. II, p. 389 (1943), a process for synthesis of phenylacetone from phenylacetic acid and acetic acid using $ThO_2$ (catalyst). The process, however, is difficult to carry out in industry because the thorium compound used as a catalyst is radioactive and its handling is restricted.

There is also reported, in German Patent No. 2758113, a process for synthesis of aliphatic or aromatic methyl ketone from carboxylic acid using $ZrO_2$ (catalyst). In the literature, synthesis of, for example, methyl n-undecyl ketone is described in Examples; however, the yield is as low as 60%.

There is also reported, in Japanese Patent Application (Laid-Open) No. 25541/1985, a process for production of ketone from aromatic or aralkyl carboxylic acid and lower fatty acid using La, Ce or Ti oxide (catalyst). For example, o-methylacetophenone is synthesized from o-toluic acid and acetic acid according to the process; however, the yield in the process is as low as 68% at the highest.

There is also reported, in Japanese Patent Application (Laid-Open) No. 175951/1989, a process for production of ketone from higher aliphatic carboxylic acid and lower aliphatic carboxylic acid using cerium oxide-on-alumina catalyst. According to the literature, methyl n-undecyl ketone, for example, is produced from lauric acid and acetic acid and the yield is 85%. In the process, however, GHSV (gas phase space velocity) is as low as 171 $hr^{-1}$; consequently, the productivity is low and a large reactor is necessary, which are not advantageous industrially.

A process for synthesis of higher ketone is known which comprises reacting a metal (e.g. Mg) or magnesium oxide with a higher fatty acid (e.g. stearic acid) at 300°–345° C. in a flask and decomposing the resulting stearic acid salt to obtain a higher ketone [J. of Soc. of Chemical Industry, Japan, 40(6), 408–410 and J. of Soc. of Chemical Industry, Japan, 40(7), 521–523]. The reaction of the process is a stoichiometric reaction in liquid phase organic synthesis and is basically different from the gas phase catalytic reaction aimed at by the present invention.

The object of the present invention is to provide a process for producing a ketone from a carboxylic acid(s) by a gas phase catalytic reaction using a catalyst, at a high yield at high productivity.

According to the present invention there is provided a process for producing a ketone represented by a general formula RCOR' (wherein R is a $C_1$–$C_{17}$ alkyl group, a $C_7$–$C_{12}$ aralkyl group, a $C_7$–$C_{12}$ aryl group or a $C_5$–$C_8$ cycloalkyl group; R' is a $C_1$–$C_{17}$ alkyl group, a $C_7$–$C_{12}$ aralkyl group, a $C_7$–$C_{12}$ aryl group or a $C_5$–$C_8$ cycloalkyl group; R and R' may the same), which process comprises reacting a carboxylic acid represented by a general formula RCOOH (wherein R has the same definition as given above) with a carboxylic acid represented by a general formula R'COOH (wherein R' has the same definition as given above) in a gas phase in the presence of a catalyst containing at least either of MgO and CaO.

Examples of the carboxylic acids used in the reaction are acetic acid, propionic acid, butyric acid, isobutyric acid, valeric acid, isovaleric acid, n-hexanoic acid, n-heptanoic acid, valproic acid, 2-ethylhexanoic acid, n-nonanoic acid, 3,5,5-trimethylhexanoic acid, n-decanoic acid, undecylic acid, lauric acid, tridecanoic acid, myristic acid, pentadecanoic acid, heptadecanoic acid and stearic acid.

An industrially preferable example of the present process is a reaction between a carboxylic acid of RCOOH (wherein R is a $C_9$–$C_{17}$ alkyl group) and a carboxylic acid of R'COOH (wherein R' is a methyl group), i.e. acetic acid. Another preferable example is a reaction between a carboxylic acid of RCOOH (wherein R is a $C_9$–$C_{17}$ alkyl group) and a carboxylic acid of R'COOH (wherein R' is a $C_9$–$C_{17}$ alkyl group).

The gas-phase catalytic reaction aimed at by the present invention is a decarboxylation reaction. It is generally thought that since an alkaline earth metal oxide generally becomes an alkaline earth metal carbonate in a decarboxylation reaction, MgO or CaO is unusable as a catalyst in the reaction. In the present process, however, MgO and CaO can both act as a catalyst by setting the reaction temperature at 250° C. or above (when a MgO-containing catalyst is used) and at 450° C. or above (when a CaO-containing catalyst is used). For example, when a reaction is conducted at a temperature of 450° C. or above using CaO as a catalyst, at the initial stage of the reaction, a ketone is formed but no $CO_2$ is formed because part of CaO is converted to $CaCO_3$. However, after this reaction has been continued for 1 hour or more and a CaO–$CaCO_3$ decomposition equilibrium has been reached, a ketone is formed by the catalysis of the CaO moiety and $CO_2$ is formed simultaneously. Interestingly, BaO, although being an alkaline earth metal oxide, shows no catalysis in the present process. The reason is that since $BaCO_3$ has a high decomposition equilibrium temperature of 1,450° C. at 1 atm., BaO is completely converted to $BaCO_3$ at a reaction temperature of, for example, 500° C. or below.

The catalyst used in the present process is not restricted to a catalyst containing at least either of MgO and CaO, and may be one obtained by adding, to the catalyst, $P_2O_5$, $Sb_2O_3$, ZnO, $Fe_2O_3$, $SnO_2$, CuO, an alkali metal oxide or the like in order to adjust the acidity or basicity of the catalyst. The catalyst of the present invention is used by loading the catalyst on a powdery carrier (e.g. SiC, α-alumina or diatomaceous earth) or on a cylindrical, spherical, ring-shaped or crushed carrier, or by molding the catalyst itself into pellets or other form.

The present invention is hereinafter described specifically by way of Examples and Comparative Examples.

The catalysts used in Examples and Comparative Examples were obtained by molding MgO or CaO (each of special grade quality) or its mixture with the above-mentioned additive (this was as necessary added for acidity or basicity adjustment) and grinding the resulting molding into 10–24 mesh. 8 cc of each ground catalyst was filled in a stainless steel tube having an inside diameter of 10 mm. The stainless steel tube was then immersed in a molten salt to set the tube at an intended reaction temperature. From the inlet of the tube and through the tube was passed a vapor of a raw material carboxylic acid(s) together with nitrogen as a carrier gas (flow rate=480 ml/min) at 1 atm. to give rise to a gas-phase catalytic reaction. The reaction mixture gas containing a reaction product and an unreacted carboxylic acid(s) was analyzed by gas chromatography using FID as a detector.

The reaction conditions and results in Examples are shown in Table 1, and the reaction conditions and results in Comparative Examples are shown in Table 2.

EXAMPLE 1

MgO was used as a catalyst. A material gas consisting of 5% by volume of n-caprylic acid as a carboxylic acid and 95% by volume of nitrogen as a carrier gas was passed at a gas hourly space velocity (GHSV) of 3,789 hr$^{-1}$ and subjected to a reaction at 420° C. The results are shown in Table 1. The conversion of carboxylic acid was 81.5%; the yield of ketones formed was 75.4%; and the selectivity of intended ketone, i.e. 8-pentadecanone was 92.5%.

In the present invention, the conversion of carboxylic acid(s), the yield of ketones and the selectivity of intended ketone are defined by the following formulas.

Conversion of carboxylic acid(s)=[(moles of material carboxylic acid(s)−moles of residual carboxylic acid(s))/(moles of material carboxylic acid(s))]×100

Yield of ketones=[(moles of formed ketones)×2/(moles of material carboxylic acid(s))]×100

Selectivity=[(moles of intended ketone)/(moles of total ketones formed)]×100

EXAMPLE 2

A reaction was conducted in the same manner as 2in Example 1 except that the catalyst was changed to CaO and the reaction temperature was changed to 480° C. The results are shown in Table 1. The conversion of carboxylic acid was 90.4%; the yield of ketones formed was 74.8%; and the selectivity of intended 8-pentadecanone was 82.7%.

Part of the CaO used as a catalyst was CaCO$_3$ after the reaction, but the change did not hinder the reaction.

EXAMPLE 3

A mixture of 2% by volume of lauric acid, 20% by volume of acetic acid and 78% by volume of nitrogen was used as a material gas, and the reaction temperature was set at 450° C. In this reaction system, acetic acid was used in excess. The results are shown in Table 1. The conversion of carboxylic acids was 88.9%; the yield of ketones based on lauric acid was 80.4%; and the selectivity of intended 2-tridecanone was 90.4%.

EXAMPLES 4-6

Example 4 is a case in which lauric acid alone was used as the carboxylic acid component; Example 5 is a case in which stearic acid and acetic acid (acetic acid was in excess) were used as the carboxylic acid component; and Example 6 is a case in which stearic acid alone was used as the carboxylic acid component. As shown in Table 1, the results of all these cases were good.

EXAMPLES 7-9

Example 7 is a case in which MgO and an additive (K$_2$O, 0.1 mole per mole of MgO) were used as the catalyst; Example 8 is a case in which MgO and an additive (ZnO, 0.1 mole per mole of MgO) were used as the catalyst; and Example 9 is a case in which CaO and an additive (P$_2$O$_5$, 0.1 mole per mole of CaO) were used as the catalyst. In all these cases in which an additive was added for acidity or basicity adjustment of catalyst, the results were good as shown in Table 1.

EXAMPLE 10

In this Example, a mixture of CaO and MgO was used as the catalyst. As shown in Table 1, the results were good also in this Example.

EXAMPLE 11

In this Example, two carboxylic acids were used; as one carboxylic acid RCOOH was used phenylacetic acid in which R is an aralkyl group, and as other carboxylic acid R'COOH was used acetic acid in which R' is a C$_1$ alkyl group (acetic acid was used in excess). As shown in Table 1, the results were good also in this Example.

In any of the above Examples, good results were obtained in a reaction using a large space velocity of 3,700 hr$^{-1}$ or more. This indicates that the present process has high productivity.

Comparative Example 1

In this Comparative Example, the same material gas as in Examples 1 and 2 was used; CeO$_2$ was used as the catalyst; and a reaction was conducted at 400° C. The results are shown in Table 2. The conversion of carboxylic acid was almost satisfactory at 79.3%; however, the yield of ketones was 49.5% and the selectivity of 8-pentadecanone was 62.4%, and both were lower than those in Examples 1 and 2. In the reaction of this Example, not only ketones but also CO$_2$ of more than stoichiometric amount were formed; further, not only intended 8-pentadecanone but also a large amount of high-boiling ketones were formed.

Comparative Example 2

In this Comparative Example, the same material gas as in Example 3 was used; ZrO$_2$ was used as the catalyst; and a reaction was conducted at 410° C. The results are shown in Table 2. The conversion of carboxylic acids was only slightly higher than that in Example 3; however, the yield of ketones was 65.1% and the selectivity of 2-tridecanone was 72.3%, and both were lower than those in Example 3. In the reaction of this Example, not only ketones but also CO$_2$ of more than stoichiometric amount were formed; further, not only intended 2-tridecanonoe but also a large amount of high-boiling ketones were formed.

Comparative Example 3

In this Comparative Example, the same catalyst and material gas as in Example 1 were used; and a reaction temperature was set at 200° C., which was lower than that in Example 1. The results are shown in Table 2. The conversion of carboxylic acid was 10.1%; the yield of ketones was 5.1%; the selectivity of 8-pentadecanone was 50.5%; all were lower than those in Example 1. This indicates that when MgO is used as a catalyst and the reaction temperature is 200° C., the catalytic activity is significantly low.

Comparative Example 4

In this Comparative Example, the same catalyst and material gas as in Example 2 were used; and a reaction temperature was set at 400° C., which was lower than that in Example 2. The results are shown in Table 2. The conversion of carboxylic acid was 31.4%; the yield of ketones was 21.6%; the selectivity of 8-pentadecanone was 68.8%; all were lower than those in Example 2. This indicates that when CaO is used as a catalyst and the reaction temperature is 400° C., the catalytic activity is significantly low.

TABLE 1

| Catalyst | | Material gas composition | | | Reaction temp. (°C.) | Conversion of carboxylic acid(s) (%) | Ketones | |
|---|---|---|---|---|---|---|---|---|
| | | Carboxylic acid(s) (vol. %) | $N_2$ (vol. %) | GHSV ($hr^{-1}$) | | | Yield (%) | Selectivity (%) |
| Example 1 | MgO | n-Caprylic acid 5 $CH_3(CH_2)_6COOH$ | 95 | 3789 | 420 | 81.5 | 75.4 8-Pentadecanone $CH_3(CH_2)_6CO(CH_2)_6CH_3$ | 92.5 |
| Example 2 | CaO | n-Caprylic acid 5 | 95 | 3789 | 480 | 90.4 | 74.8 8-Pentadecanone | 82.7 |
| Example 3 | MgO | Lauric acid 2 $CH_3(CH_2)_{10}COOH$ Acetic acid 20 | 78 | 4615 | 450 | 88.9 | 80.4 2-Tridecanone $CH_3(CH_2)_{10}COCH_3$ | 90.4 |
| Example 4 | MgO | Lauric acid 5 | 95 | 3789 | 410 | 92.0 | 69.5 12-Tricosanone $CH_3(CH_2)_{10}CO(CH_2)_{10}CH_3$ | 75.5 |
| Example 5 | CaO | Stearic acid 2 $CH_3(CH_2)_{16}COOH$ Acetic acid 20 | 78 | 4615 | 470 | 98.1 | 70.2 2-Nonadecanone $CH_3(CH_2)_{16}COCH_3$ | 71.6 |
| Example 6 | CaO | Stearic acid 5 | 95 | 3789 | 450 | 89.6 | 67.4 18-Pentatriacontanone $CH_3(CH_2)_{16}CO(CH_2)_{16}CH_3$ | 75.2 |
| Example 7 | $(MgO)_1$—$(K_2O)_{0.1}$ | Benzoic acid 5 Acetic acid 25 | 70 | 3789 | 430 | 79.5 | 69.7 Acetophenone $C_6H_5COCH_3$ | 87.7 |
| Example 8 | $(MgO)_1$—$(ZnO)_{0.1}$ | Cyclohexane-carboxylic acid 5 Acetic acid 25 | 70 | 3789 | 380 | 83.1 | 67.3 Methyl cyclohexyl Ketone $C_6H_{11}COCH_3$ | 81.0 |
| Example 9 | $(CaO)_1$—$(P_2O_5)_{0.1}$ | Isobutyric acid 5 $(CH_3)_2CHCOOH$ | 95 | 3789 | 450 | 79.8 | 65.0 2,4-Dimethyl-3-pentanone $(CH_3)_2CHCOCH(CH_3)_2$ | 81.5 |
| Example 10 | $(CaO)_1$—$(MgO)_{0.1}$ | n-Caprylic acid 5 | 95 | 3789 | 470 | 91.3 | 75.1 8-Pentadecanone | 82.3 |
| Example 11 | $(MgO)_1$—$(Sb_2O_3)_{0.1}$ | Phenylacetic acid 2 Acetic acid 20 | 78 | 4615 | 440 | 80.1 | 68.2 Methyl benzyl ketone $C_6H_5CH_2COCH_3$ | 85.1 |

TABLE 2

| Catalyst | | Material gas composition | | | Reaction temp. (°C.) | Conversion of carboxylic acid(s) (%) | Ketones | |
|---|---|---|---|---|---|---|---|---|
| | | Carboxylic acid(s) (vol. %) | $N_2$ (vol. %) | GHSV ($hr^{-1}$) | | | Yield (%) | Selectivity (%) |
| Comparative Example 1 | $CeO_2$ | n-Caprylic acid 5 | 95 | 3789 | 400 | 79.3 | 49.5 8-Pentadecanone | 62.4 |
| Comparative Example 2 | $ZrO_2$ | Lauric acid 2 Acetic acid 20 | 78 | 4615 | 410 | 90.1 | 65.1 2-Tridecanone | 72.3 |
| Comparative Example 3 | MgO | n-Caprylic acid 5 | 95 | 3789 | 200 | 10.1 | 5.1 8-Pentadecanone | 50.5 |
| Comparative Example 4 | CaO | n-Caprylic acid 5 | 95 | 3789 | 400 | 31.4 | 21.6 8-Pentadecanone | 68.8 |

As demonstrated by the above Examples and Comparative Examples, an intended ketone can be produced at a high yield at high productivity, by the present process for producing a ketone from carboxylic acid(s) in a gas phase in the presence of a catalyst containing at least either of MgO and CaO.

What is claimed is:

1. A process for producing a ketone represented by general formula RCOR', wherein R represents a $C_9$–$C_{17}$ alkyl group, or a $C_5$–$C_8$ cycloalkyl group; R' represents a $C_1$–$C_{17}$ alkyl group, a $C_6$–$C_{12}$ aryl group or a $C_5$–$C_8$ cycloalkyl group; and R and R' may be the same or different;

which process comprises, reacting a carboxylic acid represented by general formula RCOOH, wherein R has the same definition as given above, with a carboxylic acid represented by general formula R'COOH, wherein R' has the same definition as given above, in a gas phase in the presence of a catalyst containing MgO at a temperature of 250° C. or above.

2. A process for producing a ketone represented by general formula RCOR', wherein R represents a $C_9$–$C_{17}$ alkyl group, or a $C_5$–$C_8$ cycloalkyl group;

R' represents a $C_1$–$C_{17}$ alkyl group, a $C_6$–$C_{12}$ aryl group or a $C_5$–$C_8$ cycloalkyl group; and R and R' may be the same or different;

which process comprises, reacting a carboxylic acid represented by general formula RCOOH, wherein R has the same definition as given above, with a carboxylic acid represented by general formula R'COOH, wherein R' has the same definition as given above, in a gas phase at a temperature of at least 450° C. in the presence of a catalyst comprising CaO.

3. A process for producing a ketone represented by general formula RCOR' wherein R is a $C_9$–$C_{17}$ alkyl group or a $C_5$–$C_8$ cycloalkyl group;

R' is a $C_1$–$C_{17}$ alkyl group, a $C_6$–$C_{12}$ aryl group or a $C_5$–$C_8$ cycloalkyl group; and R and R' may be the same or different;

which process comprises, reacting a carboxylic acid represented by general formula RCOOH, wherein R has the same definition as given above, with a carboxylic acid represented by general formula R'COOH, wherein R' has the same definition as given above, in a gas phase in the presence of a catalyst containing MgO and CaO.

4. A process for producing a ketone represented by general formula RCOR', wherein R is a $C_9$–$C_{17}$ alkyl group or a $C_5$–$C_8$ cycloalkyl group;

R' is a $C_1$–$C_{17}$ alkyl group, a $C_6$–$C_{12}$ aryl group or a $C_5$–$C_8$ cycloalkyl group; and R and R' may be the same different, which process comprises reacting a carboxylic acid represented by general formula RCOOH, wherein R has the same definition as given above with a carboxylic acid represented by general formula R'COOH, wherein R' has the same definition as given above in a gas phase at a temperature of 450° C. or above in the presence of a catalyst containing a mixture of at least one of MgO and CaO with at least one additional metal oxide selected from the group consisting of $P_2O_5$, $Sb_2O_3$, ZnO, $Fe_2O_3$, $SnO_2$, CuO and alkali metal oxide.

5. A process according to any one of claims 1 to 14 wherein

R' is a $C_1$–$C_{17}$ alkyl group or a $C_5$–$C_8$ cycloalkyl group; and

R and R' may be the same.

6. A process according to any of claims 1 to 4, wherein R is a $C_9$–$C_{17}$ alkyl group and R' is a methyl group.

7. A process according to any of claims 1 to 4, wherein R and R' are each a $C_9$–$C_{17}$ alkyl group.

* * * * *